United States Patent [19]

Abe et al.

[11] Patent Number: 5,416,238

[45] Date of Patent: May 16, 1995

[54] L-ARGININAL ACETAL DERIVATIVES AND A PROCESS FOR PRODUCTION THEREOF

[75] Inventors: Yoshihito Abe; Akio Hashimoto, both of Koriyama; Takeshi Nagasawa, Urawa; Katsumasa Kuroiwa, Koriyama, all of Japan

[73] Assignee: Nitto Boseki Co., Ltd., Fukushima, Japan

[21] Appl. No.: 755,527

[22] Filed: Sep. 5, 1991

Related U.S. Application Data

[62] Division of Ser. No. 466,236, Jan. 17, 1990, abandoned.

[51] Int. Cl.$^6$ .............................................. C07C 209/78
[52] U.S. Cl. .......................................................... 564/240
[58] Field of Search ................................. 564/230, 240

[56] References Cited

U.S. PATENT DOCUMENTS 3,429,919  2/1969  Koopman et al. ................ 260/564
5,296,498  3/1994  Malen et al. ...................... 514/401

FOREIGN PATENT DOCUMENTS 3040993    6/1982   European Pat. Off. .
0104768A   4/1984   European Pat. Off. .
59-227855A 12/1984  Japan .

OTHER PUBLICATIONS

Carey, Francis *Organic Chemistry* McGraw-Hill Pub. (1987) p. 657.
Morrison & Boyd, *Organic Chemistry* (3rd Ed.) Allyn & Bacon, Inc. (1973) p. 641.

*Primary Examiner*—Allen J. Robinson
*Assistant Examiner*—Brian M. Burn
*Attorney, Agent, or Firm*—Darby & Darby

[57] ABSTRACT

Novel $N^G$-protected or unprotected-L-argininal-dibutyl acetals (I) can be prepared from L-argininal derivatives (III) merely by reacting in an azeotropic solvent in the presence of p-toluenesulfonic acid. In the products (I), L-form amounts to more than 99%, without further optical resolution. The L-argininal acetals (I) are useful as starting materials for preparing peptidyl-L-argininal derivatives which can provide protease inhibitors or ligands used for affinity chromatography of various proteases.

3 Claims, No Drawings

L-ARGININAL ACETAL DERIVATIVES AND A PROCESS FOR PRODUCTION THEREOF

This is a division, of application Ser. No. 466,236, filed Jan. 17, 1990, (now abandoned).

BACKGROUND OF THE INVENTION

FIELD OF THE INVENTION

The present invention relates to $N^G$-protected$^G$-protected-L-argininal-di-lower alkyl acetals represented by formula (I):

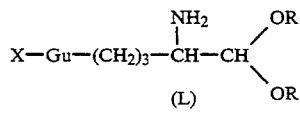

wherein X represents a protective group for a guanidino group; Gu represents a guanidine residue; and R represents a lower alkyl group, and salts thereof. The present invention also relates to L-argininal-di-lower alkyl acetals represented by formula (II):

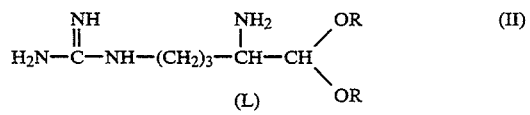

wherein R represents a lower alkyl group, and salts thereof, and a process for production thereof as well as intermediates for synthesis thereof.

The $N^G$-protected-L-argininal-di-lower alkyl acetals (I) and L-argininal-di-lower alkyl acetals (II) of the present invention are useful as starting materials for N-terminal-protected or unprotected-peptidyl-L-argininal-di-lower alkyl acetals which are starting materials for various protease inhibitors and ligands used for affinity chromatography of various proteases.

STATEMENT OF RELATED ARTS

Leupeptin was found by Umezawa et al. (The Journal of Antibiotics, 22, 283 (1969)). Since then, a variety of peptide aldehydes have been developed as protease inhibitors. However, inter alia, known N-terminal-substituted or unsubstituted peptidyl-argininals encounter serious problems in synthesis, because they have guanidino group on the side chain thereof, they are liable to racemize, they are physically unstable, DL resolution is difficult because of their equilibrated state in a solution thereof, and the like. Furthermore, $N^G$-protected-L-argininal-di-lower alkyl acetals which are expected to be used as starting materials are heretofore unknown compounds. As a relatively close compound, $N^G$-unprotected-argininal dibutyl acetal is merely known.

According to Japanese Patent Application Laid-Open No. 59-227855, there is described, for preparing D,L-argininal dibutyl acetal, a process which comprises refluxing L-leupeptin (acetyl-L-leucyl-L-leucyl-L-argininal) in benzene in the presence of butanol and reacting Pronase E ® (manufactured by Kaken Chemical Co., Ltd.) with the resulting D,L-leupeptin dibutyl acetal (acetyl-L-leucyl-L-leucyl-D,L-argininal dibutyl acetal) to obtain D,L-argininal dibutyl acetal. In this process, however, argininal dibutyl acetal is obtained as a racemic compound.

That is, any publication describing not only $N^G$-protected-L-argininal acetals but also $N^G$-protected-argininal acetals or production thereof is not found to date.

Furthermore, no method has been found for effective resolution of peptidyl-L-argininal-di-lower alkyl acetals which are useful as the starting materials of various protease inhibitors.

Furthermore, there is no known method for effective resolution of $N^G$-protected-L-argininal-di-lower alkyl acetals from the racemic compounds.

The method for synthesis of argininal dibutyl acetal described in Japanese Patent Application Laid-Open No. 59-227855 involves the following problems. (1) L-Leupeptin, which is a starting material, is expensive. (2) Only D,L-argininal dibutyl acetal is obtained from L-leupeptin, though the L-form is useful. (3) Yields in respective steps are poor. (4) Procedures for isolation are complicated. (5) It is difficult to optically resolve a mixture of D,L-argininal dibutyl acetal and a method is not known.

Furthermore, in the case of synthesizing N-terminal-protected or unprotected-peptidyl-L-argininals using this mixture as a starting material, its diastereomers may be resolved from each other by means of chromatography using silica gel as a carrier, as in N-benzyloxycarbonyl-L-prolyl-D,L-argininal dibutyl acetal; but in many cases, optical resolution is impossible as in the case of N-benzyloxycarbonyl-glycyl-D,L-argininal.

In addition, peptidyl-argininal is generally in an equilibrated state in a solution (cf. The Journal of Antibiotics, 24, 402 (1971)) and it was impossible to resolve D-form and L-form from N-terminal-protected or un-protected-peptidyl-D,L-argininals.

Therefore, it is often extremely difficult to produce N-terminal-protected or unprotected-peptidyl-L-argininals and di-lower alkyl acetals thereof from D,L-argininal-di-lower alkyl acetals obtained by semi-synthesis of L-leupeptin.

SUMMARY OF THE INVENTION

Therefore, an object of the present invention is to provide $N^G$-protected-L-argininal-di-lower alkyl acetals represented by formula (I) and L-argininal-di-lower alkyl acetals represented by formula (II) which are extremely useful as starting materials for N-terminal-protected or unprotected-peptidyl-L-argininals.

Another object of the present invention is to provide a process for producing these acetal derivatives.

A further object of the present invention is to provide a synthetic process having various advantages: (1) starting raw materials are readily available (2) it is possible to synthesize by chemical conversion using inexpensive reactants; (3) yields in the respective steps are good; (4) isolation can be effected in a simple manner; (5) the resulting compounds are L-form in greater than 99%; etc.

A further object of the present invention is to provide intermediates for synthesis used in the synthetic process.

A first aspect of the present invention thus lies in $N^G$-protected-L-argininal-di-lower alkyl acetals represented by formula (I):

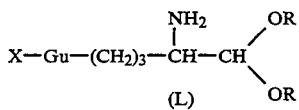

[wherein X represents a protective group for guanidino group; Gu represents a guanidine residue; and R represents a lower alkyl group] and salts thereof.

A second aspect of the present invention lies in L-argininal-di-lower alkyl acetals represented by formula (II):

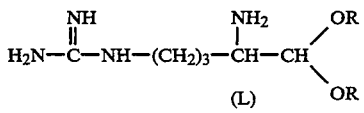

[wherein R represents a lower alkyl group] and salts thereof.

A third aspect of the present invention lies in a process for production of compounds shown by general formula (I) described above, which comprises reacting L-argininal derivatives represented by general formula (III):

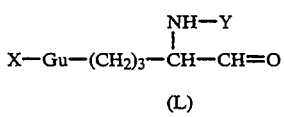

[wherein X and Gu have the same significance as defined above; and Y represents an amino protective group capable of being split off in a solvent containing an acid], in a solvent containing a lower alcohol in the presence of inorganic or organic acids.

A fourth aspect of the present invention lies in L-argininal derivatives represented by general formula (III):

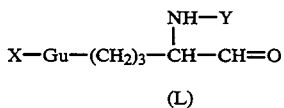

[wherein X and Gu have the same significance as defined above].

DETAILED DESCRIPTION OF THE PREFERRED EMBODIMENTS

The protective groups shown by X in general formulae (I), (II) and (III) are, for example, benzyloxycarbonyl group, dibenzyloxycarbonyl group, nitro group, p-toluenesulfonyl group and other conventional protective groups used for protecting the guanidino group.

Gu represents a guanidine residue and specific examples include:

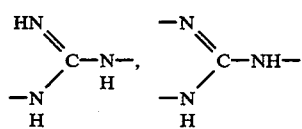

etc.

The lower alkyl group shown by R has preferably 1 to about 6 carbon atoms and specific examples include methyl, ethyl, butyl, t-butyl, pentyl, hexyl, etc.

Y in general formula (III) represents a conventional amino protective group capable of being split off in a solvent containing an acid. Specific examples of the protective group include t-butyloxycarbonyl group, t-amyloxycarbonyl group, 2-(p-biphenyl)-isopropyloxycarbonyl group, etc.

The compounds of general formulae (I) and (II) may also be in the form of salts. As such salts, there are, for example, acid addition salts with inorganic acids such as hydrochloric acid, sulfuric acid, phosphoric acid, nitric acid, etc.; or organic acids such as succinic acid, citric acid, oxalic acid, p-toluenesulfonic acid, etc.

The L-argininal derivatives represented by general formula (III) can be synthesized, for example, as follows (hereinafter X, Gu and Y have the same significance as described above).

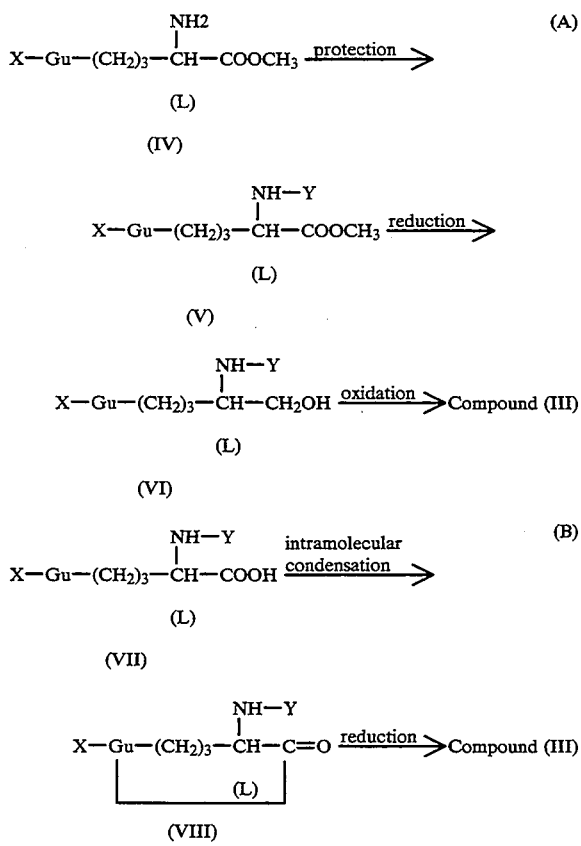

That is, Compound (III) can be obtained by first protecting the α-amino group of $N^G$-X-L-arginine methyl ester (IV) to give $N^\alpha$-Y-$N^G$-X-L-arginine methyl ester (V), reducing the resulting methyl ester (V) as a raw material with sodium borohydride by the method of Seki et al. (cf. Chemical & Pharmaceutical Bulletin, 13 (8), 995 (1965)) and then oxidizing the resulting $N^\alpha$-Y-$N^G$-X-L-argininol (VI) using sulfur trioxide-pyridine complex in anhydrous dimethylsulfoxide in the presence of amines (cf. J. Am. Chem. Soc., 89 (21), 5505 (1967)).

Compound (III) may also be synthesized by intramolecularly condensing $N^\alpha$-Y-$N^G$-X-L-arginine (VII) and reducing the resulting $N^\alpha$-Y-$N^G$-X-L-arginine lactam (VIII) with lithium aluminum hydride below −10° C.

The thus obtained Compound (III) is refluxed in a solvent containing a lower alcohol, preferably an alcohol having 1 to 6 carbon atoms, more preferably an alcohol having 4 carbon atoms, whereby acetal formation and removal of the protective group for the α-amino group occur. Thus, the $N^G$-protected-L-argininal-di-lower alkyl acetals represented by general formula (I), in which the L-form amount is greater than 99%, can be synthesized. When the protective group (X) for the guanidino group is removed from Compound (I), the L-argininal-di-lower alkyl acetal represented by general formula (II), in which the L-form amount is greater to more than 99%, can be obtained.

The acid as used herein refers to inorganic acids such as hydrochloric acid, sulfuric acid, etc.; organic acids such as p-toluenesulfonic acid, methanesulfonic acid, etc. Of these acids, p-toluenesulfonic acid is preferred. These acids are used in 1 to 5 molar equivalents, preferably 2 to 3 molar equivalents, based on Compound (III). Upon the acetalization, it is necessary to distill off the water formed. Therefore, it is preferred to use a solvent mixture of an azeotropic solvent with water such as benzene, toluene, etc. with the corresponding lower alcohol. In this case, a time period for reflux is between 30 minutes and 8 hours, preferably between 1 and 2 hours.

In order to obtain the compound of general formula (II) by removing the protective group for a guanidino group in the compound of general formula (I), catalytic hydrogenation may be performed in an alcoholic solvent such as ethanol, n-butanol, etc. in the presence of palladium black. The solvent may also be added with acids such as hydrochloric acid, sulfuric acid, p-toluenesulfonic acid, etc. In this case, the compound of general formula (II) can be obtained in the form of acid addition salts.

It has been confirmed by the following method that greater than 99% of the $N^G$-protected-L-argininal-di-lower alkyl acetal represented by formula (I) and the L-argininal-di-lower alkyl acetal represented by formula (II) are L-form.

Ishii et al. has synthesized N-benzyloxycarbonyl-L-prolyl-D,L-argininal dibutyl acetal by coupling D,L-argininal dibutyl acetal prepared from D,L-leupeptin dibutyl acetal with N-benzyloxycarbonyl-L-proline (cf. Chemical & Pharmaceutical Bulletin, 34 (4) 1748 (1986)). In thin layer chromatography using silica gel as a carrier, this diastereomic mixture gives spots showing Rf values of 0.65 and 0.56 (n-butanol: butyl acetate:acetic acid:water=4:2:1:1 (v/v)) which are positive in Sakaguchi reaction. These spots are attributable to N-benzyloxycarbonyl-L-prolyl-L-argininal dibutyl acetal and N-benzyloxycarbonyl-L-prolyl-D-argininal dibutyl acetal, respectively.

From $N^G$-protected-L-argininal-dibutyl acetal which is prepared as one embodiment of the present invention, the guanidino protective group is removed. Using the thus obtained L-argininal dibutyl acetal, N-benzyloxycarbonyl-L-prolyl-L-argininal dibutyl acetal (Rf: 0.65 by thin layer chromatography under the same conditions as described above) is prepared under similar conditions. Furthermore, using D-argininal dibutyl acetal obtained using D-arginine as a starting material in a manner similar to the case of L-argininal dibutyl acetal, N-benzyloxycarbonyl-L-prolyl-D-argininal dibutyl acetal (Rf: 0.56, under the same conditions as described above) is synthesized. Both compounds are quantitatively determined by high performance liquid chromatography. Comparison in the peak areas shown by the determination reveals that the L-form amount is greater to more than 99% in the product. Therefore, it is deduced that L-form amounts to more than 99% also in the starting $N^G$-protected-L-argininal dibutyl acetal.

In contrast, in the reaction for synthesizing D,L-leupeptin dibutyl acetal described in Japanese Patent Application Laid-Open No. 59-227855, D-leupeptin dibutyl acetal is also by-produced so that argininal dibutyl acetal obtained by cleavage with an enzyme contains remarkable amounts of D-argininal dibutyl acetal. As the result, the obtained argininal dibutyl acetal becomes DL-form.

The thus obtained $N^G$-protected-L-argininal-di-lower alkyl acetals (I) and L-argininal-di-lower alkyl acetals (II) of the present invention are useful as starting materials of N-terminal-protected or unprotected-peptidyl-L-argininal-di-lower alkyl acetals which are starting materials of various protease inhibitors and ligands used for affinity chromatography of various proteases.

To obtain these N-terminal-protected and unprotected-peptidyl-L-argininal-di-lower alkyl acetals, amino acid residues, etc. are introduced into the $N^G$-protected-L-argininal-di-lower alkyl acetals (I) and L-argininal-di-lower alkyl acetals (II) of the present invention by methods conventionally used in peptide chemistry. These conventional methods are; for example, the following:

(1) activated ester method using N-hydroxysuccinimide, p-nitrophenol, pentachlorophenol, etc.;

(2) carbodiimide method using dicyclohexylcarbodiimide, dimethylaminopropylcarbodiimide, etc.;

(3) method using condensing agents such as diphenylphosphoric acid azide, N-ethoxycarbonyl-2-ethoxydihydroquinoline, etc.;

(4) mixed acid anhydride method using isobutyl chloroformate, pivaloyl chloride, etc.;

(5) azide method; and the like.

The compounds into which residues of amino acids, etc. are introduced by the method as described above are purified by recrystallization or column chromatography using silica gel as a carrier. If necessary and desired, the protective group such as benzyloxycarbonyl group, etc. may be removed by catalytic hydrogenation using palladium black, etc. in a solvent such as methanol.

The thus obtained compounds can be converted into various protease inhibitors by hydrolyzing the acetal site into aldehyde group.

To convert the acetal moiety into an aldehyde group, hydrolysis is generally preferred. In the case of a compound that is insoluble in water, the compound may be reacted at 10° to 60° C., preferably 25° to 40° C., for several hours, in a solvent compatible with water such as methanol, ethanol, acetone, acetonitrile, dimethylformamide, etc., using acids such as hydrochloric acid, sulfuric acid, p-toluenesulfonic acid, etc. In this case, the concentration of the acid used is not particularly limited, but it is generally preferred to adjust it to a range of 0.3 to 0.5 normal. After disappearance of the starting material, confirmed by thin layer chromatography, using silica gel as a carrier, an excess of the acid is removed with a weakly basic exchange resin, e.g., Dowex ® WGR. Then freeze-drying follows to obtain salts of the desired compound.

When the $N^G$-protected-L-argininal-di-lower alkyl acetal (I) is used as a raw material for the final product, N-terminal-protected or unprotected-peptidyl-L-argininal, the conversion to an of aldehyde group may be conducted either prior to or after removal of the protective group for the guanidino group.

Hereafter the present invention is described in more detail with reference to the examples but is not deemed to be limited to these examples.

For measurement of Rf values in thin layer chromatography in the following examples and reference examples, thin layer chromatography 60F 254 plates (0.25 mm) manufactured by Merck Inc. were used, unless otherwise indicated.

EXAMPLE 1

N$^G$-Benzyloxycarbonyl-L-argininal dibutyl acetal (A) Synthesis from N$^G$-X-L-arginine methyl ester

1. N$^G$-Benzyloxycarbonyl-L-arginine methyl ester dihydrochloride

To 85.3 g (0.20 mol) of N$^\alpha$-t-butyloxy-carbonyl-N$^G$-benzyloxycarbonyl-L-arginine (Günter et al., Zeitschrift für Chemie, 13 (9), 344 (1973)) was added 100 ml of acetic acid to suspend the L-arginine. The suspension was cooled with ice water and 400 ml of 2 N hydrochloric acid-acetic acid solution was added dropwise to the suspension while stirring. The mixture was then stirred at room temperature for an hour. The resulting reaction solution was poured onto about 3 liters of diethyl ether with stirring. The white precipitate formed was recovered by filtration. After washing with about 2 liters of diethyl ether, the precipitate was dried in vacuum in the presence of phosphorus pentoxide and potassium hydroxide to give 76.9 g of white solid.

On the other hand, 150 ml of methanol was cooled to $-10°$ C. and 62.5 g of thionyl chloride was added dropwise to methanol while stirring at the same temperature. After stirring for 10 minutes, 57.2 g of the white solid previously prepared was added to the mixture under moisture-free conditions. The mixture was spontaneously elevated to room temperature and stirring was continued overnight. The solvent was distilled off from the reaction solution under reduced pressure. The residue was dissolved in 300 ml of chloroform. The solution was poured onto about 3 liters of ethyl acetate with stirring. The formed white-solid was taken by filtration. After washing with about 1 liter of ethyl acetate, the solid was dried in vacuum in the presence of phosphorus pentoxide and potassium hydroxide to give white solid.

Yield: 57.8 g (97,5%)
Melting point: 102°–105° C. (foamed)
$[\alpha]_D^{26}$: +13° (c=1, methanol)
Rf: 0.39 (n-butanol:acetic acid:water=4:1:1, v/v)

2. N$^\alpha$-t-Butyloxycarbonyl-N$^G$-benzyloxycarbonyl-L-arginine methyl ester In 200 ml of methylene chloride was dissolved 39.5 g (0.10 mol) of N$^G$-benzyloxycarbonyl-L-arginine methyl ester dihydrochloride (1). The solution was cooled to 0° C. and 27.8 ml of triethylamine was added. After stirring for 10 minutes, 26.5 g of S-t-butyloxycarbonyl-4,6-dimethyl-2-thiopyrimidine was added followed by stirring overnight. After washing the obtained reaction solution, in succession, with 5% hydrochloric acid (100 ml×3), saturated sodium chloride aqueous solution (100 ml×1), saturated sodium hydrogencarbonate aqueous solution (100 ml×3) and saturated sodium chloride aqueous solution (100 ml×2), the reaction solution was dried over anhydrous magnesium sulfate and the solvent was distilled off under reduced pressure. The residue obtained recrystallized from ethyl acetate and diethyl ether. The crystals were taken out by filtration and dried in vacuum to give white crystals.

Yield: 25.8 g (61.0%)
Melting point: 62°–65° C. (foamed)
$[\alpha]_D^{28}$: −8.0° (c=1, methanol)
Rf: 0.40 (chloroform:methanol=10:1, v/v)

3. N$^\alpha$-t-Butyloxycarbonyl-N$^G$-benzyloxycarbonyl-L-argininol

In 500 ml of methanol was dissolved 21.1 g of N$^\alpha$-t-butyloxycarbonyl-N$^G$-benzyloxycarbonyl-L-arginine methyl ester (2). On the other hand, 18.9 g of sodium borohydride was dissolved in 100 ml of water and the solution was dropwise added with stirring to the methanol solution previously prepared, while cooling with ice water. Stirring was continued for 4 hours at room temperature. After disappearance of the raw materials was confirmed by thin layer chromatography, using silica gel as a carrier, acetic acid was added until no gas generated. The solvent was removed from the solution by distillation under reduced pressure. 750 ml of ethyl acetate and 50 ml of water were added to the residue for extraction. After washing successively with 5% hydrochloric acid (200 ml×2), saturated sodium chloride aqueous solution (200 ml×1), saturated sodium hydrogencarbonate aqueous solution (200 ml×2) and saturated sodium chloride aqueous solution (200 ml×2), the ethyl acetate phase was dried over anhydrous magnesium sulfate and the solvent was distilled off under reduced pressure. The residue obtained was recrystallized from chloroform, ethyl acetate and diethyl ether. The crystals were recovered by filtration and dried in vacuum to give white crystals.

Yield: 16.2 g (82.0%)
Melting point: 76°–78° C.
$[\alpha]_D^{28}$: −6.0° (c=1, methanol)
Rf: 0.42 (n-butanol:butyl acetate:acetic acid:water=8:8:1:1, v/v)

4. N-t-Butyloxycarbonyl-N$^G$-benzyloxycarbonyl-L-argininal

In nitrogen atmosphere, 12.73 g of sulfur trioxide-pyridine complex was dissolved in 80 ml of absolute dimethylsulfoxide. On the other hand, 7.89 g of N$^\alpha$-t-butyloxycarbonyl-N$^G$-benzyloxycarbonyl-L-argininol (3) was dissolved in 80 ml of absolute dimethylsulfoxide in nitrogen atmosphere. The solution was cooled to 18° C. and then, while stirring at the same temperature, 11.2 ml of triethylamine and the previously prepared sulfur trioxide-pyridine complex solution were added to the solution. Stirring was continued for 20 minutes. When the resulting reaction solution was poured onto 800 ml of chilled water, a suspension was obtained. To the suspension were added 500 ml of ethyl acetate and sodium chloride for extraction. The ethyl acetate phase was successively washed with 10% citric acid aqueous solution (200 ml×saturated sodium chloride aqueous solution (200 ml×1), saturated sodium hydrogencarbonate aqueous solution (200 ml×2) and saturated sodium chloride aqueous solution (200 ml×2). The solution was dried over anhydrous magnesium sulfate and the solvent was distilled off under reduced pressure. The obtained residue was dissolved in diethyl ether and, n-hexane was added to the solution to effect crystallization. The crystals were recovered by filtration and dried in vacuum to give white crystals.

Yield: 5.2 g (66%)
Melting point: 80°–84° C. (foamed)
$[\alpha]_D^{28}$: +17° (c=1, dimethylformamide)
Rf: 0.52 (chloroform:methanol:acetic acid:water=80:20:2.5:5, v/v)
Elemental analysis for $C_{19}H_{28}N_4O_5$ (392.46) Calcd. C: 58.15% H: 7.19% N: 14.28% Found C: 58.04% H: 7.46% N: 13.98%

5. $N^G$-Benzyloxycarbonyl-L-argininal dibutyl acetal

In 25 ml of n-butanol and 100 ml of benzene were dissolved 3.92 g of $N^\alpha$-t-butyloxycarbonyl-$N^G$-benzyloxycarbonyl-L-argininal (4) and 3.99 g of p-toluenesulfonic acid monohydrate. The solution was heated to reflux for an hour while azeotropically removing the formed water using a device of Dean-Stark. The solvent was removed from the solution by distillation under reduced pressure. The resulting residue was dissolved in 100 ml of ethyl acetate. After washing with 50 ml of water, the ethyl acetate phase was dried over anhydrous magnesium sulfate and the solvent was again distilled off under reduced pressure. The residue was subjected to column chromatography using silica gel as a carrier and developed by chloroform:methanol=15:1 (v/v). The fraction showing Rf: 0.51 (n-butanol:butyl acetate:acetic acid:water=4:2:1:1, v/v) which was positive in the ninhydrin reaction, was concentrated under reduced pressure. The residue was dissolved in 100 ml of diethyl ether. After washing successively with saturated sodium hydrogencarbonate aqueous solution (50 ml×3) and saturated sodium chloride aqueous solution (50 ml×2), the solution was dried over anhydrous magnesium sulfate and the solvent was distilled off under reduced pressure. The concentrate was recrystallized from diethyl ether and n-hexane. The crystals were recovered by filtration and dried in vacuum to give white crystals.

Yield: 2.25 g (53%)
Melting point: 69°–70° C.
$[\alpha]_D^{28}$: +6.5° (c =1, acetic acid)
Rf: 0.51 (n-butanol:butyl acetate:acetic acid:water=4:2:1:1, v/v)
Elemental analysis for $C_{22}H_{38}N_4O_4 \cdot \frac{1}{2}H_2O$ (431.58)
Calcd. C: 61.23% H: 9.11% N: 12.98% Found C: 61.31% H: 9.18% N: 13.14%

(B) Synthesis from $N^\alpha$-Y-$N^G$-X-L-arginine lactam

1. $N^\alpha$-t-Butyloxycarbonyl-$N^G$-benzyloxycarbonyl-L-arginine lactam

In 1 liter of tetrahydrofuran were dissolved 13.2 g (0.50 mol) of $N^\alpha$-t-butyloxycarbonyl-$N^G$-benzyloxycarbonyl-L-arginine and 57.5 g (0.50 mol) of N-hydroxysuccinimide. The solution was cooled to 0° C. Then, while stirring at the same temperature, a solution of 103.2 g (0.50 mol) of dicyclohexylcarbodiimide in 500 ml of tetrahydrofuran was added to the solution. The temperature of the mixture was spontaneously elevated to room temperature and stirring was continued overnight. The formed dicyclohexylurea was removed by filtration. The filtrate was poured onto 3.5 liters of ice water and the precipitates were recovered by filtration. After washing with 300 ml of cold water, the crystals were dried in vacuum in the presence of phosphorus pentoxide to give white crystals.

Yield: 187.0 g (95.8%)
Melting point: 164°–165° C.
$[\alpha]_D^{26}$: −25° (c=1, tetrahydrofuran)
Rf: 0.67 (chloroform:methanol=30:1, v/v)
Elemental analysis for $C_{19}H_{26}N_4O_5$ (390.44) Calcd. C: 58.45% H: 6.71% N: 14.35% Found C: 58.29% H: 6.88% N: 14.06%

2. $N^\alpha$-t-Butyloxycarbonyl-$N^G$-benzyloxycarbonyl-L-argininal

In 1.5 liter of anhydrous tetrahydrofuran was dissolved 117.1 g (0.30 mol) of $N^\alpha$-t-butyloxycarbonyl-$N^G$-benzyloxycarbonyl-L-arginine lactam (1). The solution was cooled to −30° C. and then, while stirring at the same temperature, a solution of 11.4 g of lithium aluminum hydride in 750 ml of anhydrous tetrahydrofuran was added dropwise to the solution at −30° C. After completion of the dropwise addition, stirring was continued at −30° C. for an hour. Under cooling, 1 N sulfuric acid was added to the resulting solution to render pH 2 to 3 and, 2 liters of water was added thereto for dilution. After extracting twice with 1.5 liter of n-hexane, extraction was performed from the aqueous tetrahydrofuran phase twice with 1.5 liter of methylene chloride. The methylene chloride phase was successively washed with water (300 ml×2), 5% sodium hydrogencarbonate aqueous solution (300 ml×2) and water (300 ml×2). The solution was then dried over anhydrous magnesium sulfate and the solvent was distilled off under reduced pressure. The residue obtained was dissolved in 250 ml of diethyl ether and the solution was poured onto 2 liters of n-hexane to cause crystallization. The crystals were recovered by filtration and dried in vacuum to give white crystals.

Yield: 92.1 g (78.2%)

3. $N^G$-Benzyloxycarbonyl-L-argininal dibutyl acetal $N^\alpha$-t-Butyloxycarbonyl-$N^G$-benzyloxycarbonyl-L-argininal (2) was treated in a manner similar to (A) 5 to give $N^G$-benzyloxycarbonyl-L-argininal dibutyl acetal.

Example 2 L-Argininal dibutyl acetal hydrochloride

In 30 ml of n-butanol was dissolved 1.27 g of $N^G$-benzyloxycarbonyl-L-argininal dibutyl acetal (Example 1 (A) 5) and 1.12 ml of 2.7 N hydrochloric acid dioxane solution was added to the solution. After 0.5 g of palladium black was added to the mixture, catalytic hydrogenation was carried out. After disappearance of the raw materials was confirmed by thin layer chromatography using silica gel as a carrier, palladium black was removed by filtration and the solvent was distilled off from the filtrate under reduced pressure. The resulting concentrate was recrystallized from methylene chloride and ethyl acetate. The crystals were taken out by filtration and dried in vacuum to give white crystals.

Yield: 0.87 g (89%)
Melting point: 127°–128° C.
$[\alpha]_D^{28}$: +12.5° (c =0.8, acetic acid)
Rf: 0.51 (n-butanol:butyl acetate:acetic acid: water=2:1:1:1, v/v)
Elemental analysis for $C_{14}H_{33}N_4O_2Cl \cdot \frac{1}{2}H_2O$ (333.91)
Calcd. C: 50.36% H: 10.26% N: 16.78%
Found C: 50.53% H: 10.60% N: 16.70%
MS: m/z 289 (MH+)

Example 3 L-Argininal dibutyl acetal sulfate

In 7.5 ml of n-butanol was dissolved 0.21 g of $N^G$-benzyloxycarbonyl-L-argininal dibutyl acetal (Example 1 (A) 5) and 0.25 ml of 2 N sulfuric acid-n-butanol solution was added to the solution. After 0.5 g of palladium black was added to the mixture, catalytic hydrogenation was carried out. After disappearance of the raw materials was confirmed by thin layer chromatography, using silica gel as a carrier, 10 ml of methanol was added to remove palladium black by filtration. The solvent was distilled off from the filtrate under reduced pressure. Diethyl ether was added to the resulting concentrate. The crystals were recovered by filtration and dried in vacuum to give white crystals.

Yield: 0.11 g (65%)
Melting point: 193°–196° C. (decomposed)
$[\alpha]_D^{26}$: +7.0° (c=1, acetic acid)
Rf: 0.51 (n-butanol:butyl acetate:acetic acid:water=2:1:1:1, v/v)
MS: m/z 289 (MH+)

Example 4 L-Argininal dibutyl acetal

In 15 ml of n-butanol was dissolved 0.42 g of $N^G$-benzyloxycarbonyl-L-argininal dibutyl acetal (Example 1 (A) 5) and 0.5 g of palladium black was added to the solution to perform catalytic hydrogenation. The reaction mixture was treated in a manner similar to Example 1 (B) 2. Recrystallization from dichloromethane, ether and n-hexane gave white crystals.

Yield: 0.20 g (69%)
Melting point: 80°–82° C.
$[\alpha]_D^{26}$: +7.0° (c=1, acetic acid)
Rf: 0.51 (n-butanol:butyl acetate:acetic acid:water=2:1:1:1, v/v)
MS: m/z 289 (MH+)

Example 5 Measurement of optical purity of L-argininal dibutyl acetal hydrochloride With reference to the Ishii et al's report (supra) on the synthesis of N-benzyloxycarbonyl-L-prolyl-D,L-argininal dibutyl acetal, N-benzyloxycarbonyl-L-prolyl-L-argininal dibutyl acetal (hereinafter merely referred to as L-form (V)) (Rf: 0.65; n-butanol:butyl acetate:acetic acid:water=4:2:1:1, v/v) was obtained from L-argininal dibutyl acetal hydrochloride (Example 2) and N-benzyloxycarbonyl-L-proline-N-hydroxysuccinimide ester. On the other hand, N-benzyloxycarbonyl-L-prolyl-D-argininal dibutyl acetal (hereinafter merely referred to as D-form (VI)) (Rf: 0.56, under the same conditions as described above) was obtained from D-argininal dibutyl acetal hydrochloride synthesized using D-arginine (manufactured by Peptide Research Institute) in a manner similar to Example 1 (A) 1 to 5 and Example 2.

The synthesized compounds were analyzed by high performance liquid chromatography (column: YMC AM-303 ODS (manufactured by Yamamura Chemical Research Institute), moving phase: 0.05 M sodium dihydrogen-phosphate:acetonitrile:methanol=60:40:9, flow rate: 1.0 ml/min, wavelength measured: 205 nm) according to a method similar to Ishii et al. The L-form (V) and D-form (VI) were eluted, showing the peaks having retention time of 28.3 minutes and 33.2 minutes, respectively. Even though measurement was made on the unpurified L-form (V) after the coupling reaction, the peak area corresponding to the D-form (VI) was less than 1% of the area corresponding to the L-form (V). Accordingly, more than 99% of the argininal dibutyl acetal hydrochloride was the L-form.

Reference Example 1 D,L-Leupeptin dibutyl acetal sulfate

In a solvent mixture containing 5 ml of butanol and 10 ml of benzene was dissolved 0.20 g (0.4 mmol) of leupeptin sulfate (manufactured by Peptide Research Institute) and, 0.02 g of p-toluenesulfonic acid hydrate was added to the solution. The mixture was heated to reflux for 6 hours. The resulting mixture was concentrated under reduced pressure. Ethyl acetate and ethyl ether were added to the residue and the formed precipitates formed was recovered out by filtration. Then the precipitates was dried in vacuum to give 0.22 g of white solid containing D,L-leupeptin dibutyl acetal sulfate.

The acetal mixture was quantitatively determined by high performance liquid chromatography under the same conditions as in Example 5. The peak area ratio of the D-form to the L-form was approximately 1:2.

Reference Example 2 Synthesis of L-leupeptin

In 25 ml of dimethylformamide was dissolved 2.65 g of N-benzyloxycarbonyl-L-leucine. After cooling to −15° C., 1.10 ml of N-methylmorpholine and then 1.37 ml of isobutyl chloroformate were added to the solution while stirring the solution at the same temperature. The mixture was sitrred at −15° C. for 5 minutes. On the other hand, 3.25 g of L-argininal dibutyl acetal hydrochloride (Example 2) was dissolved in 30 ml of dimethylformamide and 1.40 ml of triethylamine was added to the solution. The resulting solution was dropwise added at −10° C. to the mixed acid anhydride suspension which had been previously prepared. Stirring was continued at the same temperature for an hour and then at 0° C. for an hour. The resulting reaction solution was concentrated under reduced pressure and the residue was dissolved in 100 ml of chloroform. The solution was washed successively with 10% citric acid aqueous solution (30 ml×2), saturated sodium chloride aqueous solution (30 ml×1), saturated sodium hydrogencarbonate aqueous solution (30 ml×2) and saturated sodium chloride aqueous solution (30 ml×2). After drying over anhydrous magnesium sulfate, the solvent was distilled off under reduced pressure. The obtained residue was subjected to column chromatography using silica gel as a carrier and developed with chloroform:methanol=20:1 (v/v). The fraction showing Rf: 0.48 (under the same conditions as in Example 1 (A) 4) which was positive in the Sakaguchi reaction, was concentrated under reduced pressure to give 3.73 g of N-benzyloxycarbonyl-L-leucyl-L-argininal dibutyl acetal.

In 100 ml of methanol was dissolved 3.73 g of N-benzyloxycarbonyl-L-leucyl-L-argininal dibutyl acetal obtained. In nitrogen atmosphere, 1 g of palladium black was added to the solution and the mixture was subjected to catalytic hydrogenation at room temperature for 2 hours. After palladium black was removed by filtration, the filtrate was concentrated under reduced pressure to give 2.75 g of L-leucyl-L-argininal dibutyl acetal.

After 2.75 g of L-leucyl-L-argininal dibutyl acetal obtained was coupled with N-benzyloxycarbonyl-L-leucine by the mixed acid anhydride method as described above, the coupling product was subjected to catalytic hydrogenation to give L-leucyl-L-leucyl-L-argininal dibutyl acetal.

After 0.32 g of L-leucyl-L-leucyl-L-argininal dibutyl acetal obtained was dissolved in 10 ml of dimethylformamide, 10 ml of water and 2.05 g of 1-acetylimidazole were added to the solution to render pH of the solution 8 to 9. Stirring was continued for 3 days. The solvent was distilled off from the reaction solution under reduced pressure. The residue was subjected to column chromatography using silica gel as a carrier and developed with chloroform:methanol:acetic acid:-water=80:10:2.5:5, v/v. The fraction showing, Rf: 0.35 (under the same conditions as in Example 1 (A) 4), which was positive in the Sakaguchi reaction, was concentrated under reduced pressure to give 0.14 g of N-acetyl-L-leucyl-L-leucyl-L-argininal dibutyl acetal (L-leupeptin dibutyl acetal).

The acetal was quantitatively determined by high performance liquid chromatography under the same conditions as in Example 5. Unlike Reference Example 1, no N-acetyl-L-leucyl-L-leucyl-D-argininal dibutyl acetal (D-leupeptin dibutyl acetal) was contained.

After 0.12 g of L-leupeptin dibutyl acetal obtained was dissolved in a solvent mixture containing 15 ml of 1 N hydrochloric acid and 30 ml of acetonitrile, the solution was heated at 37° C. for 2 hours. To the resulting reaction solution was added weakly basic ion exchange resin Dowex ® WGR (manufactured by Dowex Co.) to render pH 4.8. After the resin was filtered off, acetonitrile was distilled off from the filtrate under reduced pressure. The obtained solution was freeze-dried to give 38 mg of L-leupeptin.

The thus synthesized L-leupeptin showed the same spots (Rf: 0.5 to 0.65; n-butanol:acetic acid:-water=4:1:1, v/v) as those of commercially available leupeptin (manufactured by Peptide Research Institute) in thin layer chromatography using silica gel as a carrier. In addition, 50% inhibitory concentration (IC$_{50}$) of plasmin activity determined using the synthetic substrate measured according to the method described in Japanese Patent Application No. 62-274896 was also identical.

As shown in Reference Example 2, the L-argininal derivatives having the desired amino acid sequence can be obtained by the use of L-argininal-di-lower alkyl acetals as starting materials.

Therefore, the present invention can provide excellent starting materials which give the L-argininal derivatives useful as various protease inhibitors without requiring optical resolution and the process for producing the same.

What is claimed is:

1. A process for producing an N$^G$-protected-L-argininal-di-lower alkyl acetal represented by formula (I):

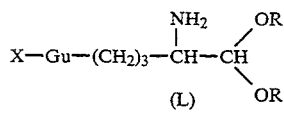

wherein X represents a protecting group for a guanidino group selected from the group consisting of a benzyloxycarbonyl group, a dibenzyloxycarbonyl group, a nitro group and a p-toluenesulfonyl group; Gu represents a guanidine residue; and R represents a lower alkyl group, or a salt thereof; which comprises: reacting an alcohol having the formula ROH, in the presence of an acid, with an L-argininal derivative represented by general formula (III):

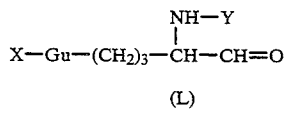

wherein X represents a protecting group for a guanidino group as defined above; Gu represents a guanidine residue; and R represents a lower alkyl group; and Y represents an amino protecting group capable of being split off in a solvent containing an acid or in a solvent containing a lower alcohol in the presence of an acid.

2. A process according to claim 1, wherein said lower alcohol is a lower alcohol having 1 to 6 carbon atoms.

3. A process according to claim 1, wherein said acid is an inorganic acid selected from the group consisting of hydrochloric acid and sulfuric acid or an organic acid selected from the group consisting of p-toluen-sulfonic acid and methanesulfonic acid.

* * * * *

UNITED STATES PATENT AND TRADEMARK OFFICE
CERTIFICATE OF CORRECTION

PATENT NO.   : 5,416,238
DATED        : May 16, 1995
INVENTOR(S)  : Yoshihito ABE, Akio HASHIMOTO, Takeshi NAGASAWA
               and Katsumasa KUROIWA It is certified that error appears in the above-indentified patent and that said Letters Patent is hereby corrected as shown below:

On the title page, item:
[30] Foreign Application Priority Data
   Jan. 18, 1989 [JP] Japan..................01-008963

Signed and Sealed this

Third Day of October, 1995

Attest:

BRUCE LEHMAN

Attesting Officer

Commissioner of Patents and Trademarks